(12) United States Patent
Jang

(10) Patent No.: US 11,890,081 B2
(45) Date of Patent: Feb. 6, 2024

(54) APPARATUS AND METHOD FOR ESTIMATING BLOOD PRESSURE

(71) Applicant: SAMSUNG ELECTRONICS CO., LTD., Suwon-si (KR)

(72) Inventor: Dae Geun Jang, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 921 days.

(21) Appl. No.: 16/595,714

(22) Filed: Oct. 8, 2019

(65) Prior Publication Data
US 2020/0221960 A1 Jul. 16, 2020

(30) Foreign Application Priority Data
Jan. 11, 2019 (KR) .................. 10-2019-0004015

(51) Int. Cl.
A61B 5/021 (2006.01)
A61B 5/00 (2006.01)

(52) U.S. Cl.
CPC ........ *A61B 5/02108* (2013.01); *A61B 5/7239* (2013.01); *A61B 5/7242* (2013.01); *A61B 5/7278* (2013.01); *A61B 2560/0223* (2013.01)

(58) Field of Classification Search
CPC . A61B 5/02108; A61B 5/7239; A61B 5/7242; A61B 5/7278; A61B 2560/0223
See application file for complete search history.

(56) References Cited

U.S. PATENT DOCUMENTS

| | | | |
|---|---|---|---|
| 8,050,730 B2 | 11/2011 | Zhang et al. | |
| 8,814,800 B2 | 8/2014 | Fortin et al. | |
| 10,045,700 B2 | 8/2018 | Noh et al. | |
| 10,448,848 B2 | 10/2019 | Park et al. | |
| 11,517,211 B2 | 12/2022 | Park et al. | |
| 2013/0324859 A1 | 12/2013 | Park et al. | |
| 2014/0278229 A1* | 9/2014 | Hong | A63B 71/06 702/160 |
| 2016/0058300 A1 | 3/2016 | Yoon et al. | |
| 2016/0242672 A1 | 8/2016 | Mikoshiba et al. | |

(Continued)

FOREIGN PATENT DOCUMENTS

| | | |
|---|---|---|
| JP | WO2015/056434 A1 | 4/2015 |
| KR | 2002-0002450 A | 1/2002 |

(Continued)

OTHER PUBLICATIONS

Xing et al. (Optical blood pressure estimation with photoplethysmography and FFT-based neural networks; vol. 7, No. 8 | Aug. 1, 2016 | Biomedical Optics Express 3007 ) (Year: 2016).*

(Continued)

*Primary Examiner* — Jay B Shah
(74) *Attorney, Agent, or Firm* — Sughrue Mion, PLLC

(57) ABSTRACT

An apparatus for estimating blood pressure, includes a pulse wave sensor configured to measure a first pulse wave signal from a user, and a processor configured to differentiate or integrate the measured first pulse wave signal to obtain a reference signal, correct the measured first pulse wave signal, based on the obtained reference signal, to obtain a second pulse wave signal, and estimate the blood pressure, based on the obtained second pulse wave signal.

20 Claims, 11 Drawing Sheets

(56) References Cited

U.S. PATENT DOCUMENTS

| | | | |
|---|---|---|---|
| 2016/0249820 A1 | 9/2016 | Puig et al. | |
| 2017/0360351 A1 | 12/2017 | Unni et al. | |
| 2018/0177413 A1 | 6/2018 | Kwon et al. | |
| 2020/0054290 A1 | 2/2020 | Jang et al. | |

FOREIGN PATENT DOCUMENTS

| | | |
|---|---|---|
| KR | 10-2006-0081178 A | 7/2006 |
| KR | 10-2012-0058243 A | 6/2012 |
| KR | 10-2016-0028303 A | 3/2016 |
| KR | 10-2017-0019189 A | 2/2017 |
| KR | 10-2017-0041117 A | 4/2017 |
| KR | 10-1724282 B1 | 4/2017 |
| KR | 10-2018-0076050 A | 7/2018 |
| KR | 10-2020-0021208 A | 2/2020 |

OTHER PUBLICATIONS

Office Action dated Nov. 28, 2023, Issued by Korean Patent Office in Korean Patent Application No. 10-2019-0004015.

\* cited by examiner

APPARATUS AND METHOD FOR ESTIMATING BLOOD PRESSURE

CROSS-REFERENCE TO RELATED APPLICATION

This application claims priority from Korean Patent Application No. 10-2019-0004015, filed on Jan. 11, 2019, in the Korean Intellectual Property Office, the disclosure of which is incorporated herein by reference in its entirety.

BACKGROUND

1. Field

Apparatuses and methods consistent with embodiments relate to an apparatus and a method for continuously estimating blood pressure based on a pulse wave signal without using a cuff.

2. Description of the Related Art

Recently, with the aging population, soaring medical costs, and a lack of medical personnel for specialized medical services, research is being actively conducted on IT-medical convergence technologies, in which IT technology and medical technology are combined. Particularly, monitoring of the health condition of the human body is not limited to places such as hospitals, but is expanding to mobile healthcare fields that may monitor a user's health state anywhere and anytime in daily life at home or office. Examples of bio-signals, which indicate the health condition of individuals, include an electrocardiography (ECG) signal, a photoplethysmogram (PPG) signal, an electromyography (EMG) signal, and the like, and various bio-signal sensors are being developed to measure these signals in daily life. Particularly, a PPG sensor may estimate blood pressure of a human body by analyzing a shape of pulse waves that reflect a cardiovascular state and the like.

SUMMARY

According to embodiments, there is provided an apparatus for estimating blood pressure, the apparatus including a pulse wave sensor configured to measure a first pulse wave signal from a user, and a processor configured to differentiate or integrate the measured first pulse wave signal to obtain a reference signal, correct the measured first pulse wave signal, based on the obtained reference signal, to obtain a second pulse wave signal, and estimate the blood pressure, based on the obtained second pulse wave signal.

The processor may be further configured to divide an amplitude of the measured first pulse wave signal by an amplitude of the obtained reference signal, to normalize the amplitude of the measured first pulse wave signal, and adjust an offset of the first pulse wave signal of which the amplitude is normalized, based on a predetermined reference point of the first pulse wave signal of which the amplitude is normalized, to obtain the second pulse wave signal.

The predetermined reference point may include any one or any combination of a point of mean arterial pressure (MAP), a point of systolic blood pressure (SBP), and a point of diastolic blood pressure (DBP) of the first pulse wave signal of which the amplitude is normalized.

The processor may be further configured to obtain a feature for estimating the blood pressure, from the obtained second pulse wave signal, and normalize the obtained feature, using a reference feature that is obtained at a time of calibration of the apparatus.

The processor may be further configured to obtain a feature for systolic blood pressure (SBP), based on a difference between a point of the SBP and a point of mean arterial pressure (MAP) of the obtained second pulse wave signal, and obtain a feature for diastolic blood pressure (DBP), based on a difference between the point of the MAP and a point of the DBP of the obtained second pulse wave signal.

The processor may be further configured to obtain a variation in the blood pressure, based on the normalized feature, and estimate the blood pressure, based on the obtained variation in the blood pressure.

The processor may be further configured to multiply a difference between a reference systolic blood pressure (SBP) and a reference mean arterial pressure (MAP) by a normalized feature for SBP of the obtained second pulse wave signal, to obtain a variation in the SBP, and multiply a difference between the reference MAP and a reference diastolic blood pressure (DBP) by a normalized feature for DBP of the obtained second pulse wave signal, to obtain a variation in the DBP.

The processor may be further configured to estimate the blood pressure, based on the obtained variation in the blood pressure and a reference mean arterial pressure (MAP) at the time of the calibration of the apparatus.

The processor may be further configured to obtain a mean arterial pressure (MAP) estimation value at a time of estimating the blood pressure, and estimate the blood pressure, based on the obtained MAP estimation value and the obtained variation in the blood pressure.

The processor may be further configured to monitor whether calibration of the apparatus is to be performed, and based on the calibration being monitored to be performed, obtain a reference feature.

According to embodiments, there is provided an apparatus for estimating blood pressure, the apparatus including a pulse wave sensor configured to measure a first pulse wave signal from a user, and a processor configured to differentiate or integrate the measured first pulse wave signal to obtain a reference signal, correct the measured first pulse wave signal, based on the obtained reference signal, to obtain a second pulse wave signal, obtain a feature associated with pulse pressure (PP), based on the obtained second pulse wave signal, and estimate the blood pressure, based on the obtained feature associated with the PP.

The processor may be further configured to divide an amplitude of the measured first pulse wave signal by an amplitude of the obtained reference signal, to normalize the amplitude of the measured first pulse wave signal, and obtain the second pulse wave signal, based on the first pulse wave signal of which the amplitude is normalized.

The processor may be further configured to normalize the obtained feature associated with the PP, using a reference feature associated with pulse pressure at a time of calibration of the apparatus.

The processor may be further configured to estimate the PP, based on the normalized feature associated with the PP and the pulse pressure at the time of calibration of the apparatus.

The processor may be further configured to obtain a mean arterial pressure (MAP) estimation value at a time of estimating the blood pressure, and estimate the blood pressure, based on the obtained MAP estimation value and the estimated PP.

The processor may be further configured to obtain a feature for systolic blood pressure (SBP) and a feature for diastolic blood pressure (DBP), based on the obtained second pulse wave signal, and obtain the feature associated with the PP, based on the obtained feature for the SBP and the obtained feature for the DBP.

According to embodiments, there is provided a method of estimating blood pressure, the method including measuring a first pulse wave signal from a user, differentiating or integrating the measured first pulse wave signal to obtain a reference signal, correcting the measured first pulse wave signal, based on the obtained reference signal, to obtain a second pulse wave signal, and estimating the blood pressure, based on the obtained second pulse wave signal.

The method may further include dividing an amplitude of the measured first pulse wave signal by an amplitude of the obtained reference signal, to normalize the amplitude of the measured first pulse wave signal. The correcting of the measured first pulse wave signal may include adjusting an offset of the first pulse wave signal of which the amplitude is normalized, based on a predetermined reference point of the first pulse wave signal of which the amplitude is normalized, to obtain the second pulse wave signal.

The method may further include obtaining a feature for estimating the blood pressure, from the obtained second pulse wave signal, and normalizing the obtained feature, using a reference feature that is obtained at a time of calibration.

The method may further include obtaining a variation in the blood pressure, based on the normalized feature. The estimating of the blood pressure may include estimating blood pressure, based on the obtained variation in the blood pressure.

DETAILED DESCRIPTION

Figure 1:
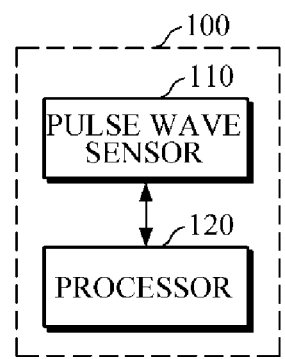
FIG. 1 is a block diagram illustrating an apparatus for estimating blood pressure according to embodiments.

Details of embodiments are included in the following detailed description and drawings. Advantages and features of the embodiments, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms first, second, etc. may be used herein to describe various elements, these elements may not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'part' or 'module', etc., may be understood as a unit that performs at least one function or operation and that may be embodied as hardware, software, or a combination thereof.

Hereinafter, embodiments of an apparatus and method for estimating blood pressure will be described in detail with reference to the accompanying drawings.

FIG. 1 is a block diagram illustrating an apparatus 100 for estimating blood pressure according to embodiments. The blood pressure estimating apparatus 100 may be embedded in a terminal, such as a smartphone, a tablet PC, a desktop computer, a laptop computer, and the like, or may be manufactured as an independent hardware device. In this case, the independent hardware device may be a wearable device worn on an object, and examples of the wearable device may include a wristwatch-type wearable device, a bracelet-type wearable device, a wristband-type wearable device, a ring-type wearable device, a glasses-type wearable device, a headband-type wearable device, or the like, but the device is not limited thereto.

Referring to FIG. 1, the blood pressure estimating apparatus 100 includes a pulse wave sensor 110 and a processor 120.

The pulse wave sensor 110 may include a sensor that may obtain volume waves such as photoplethysmogram (PPG), impedance plethysmogram (IPG), video plethysmogram (VPG), and the like. For example, the pulse wave sensor 110, which measures a PPG signal, may include a light source for emitting light onto an object, and a detector for detecting light scattered or reflected from the object. In this case, the light source may include a light emitting diode (LED), a laser diode, a fluorescent body, and the like. Further, the detector may include a photo diode, an image sensor, and the like, but is not limited thereto. The light source and/or the detector may be formed as two or more arrays, and each of the light sources may emit light of different wavelengths.

Upon receiving a request for estimating blood pressure from a user, or if criteria for estimating blood pressure are satisfied, the processor 120 may control the pulse wave sensor 110.

The processor 120 may receive a pulse wave signal from the pulse wave sensor 110, and may estimate blood pressure based on the received pulse wave signal. Once the pulse wave sensor 110 measures a first pulse wave signal for estimating blood pressure, the processor 120 may obtain a second pulse wave signal by compensating for a change in amplitude of a volume waveform, which is changed by factors other than blood pressure, e.g., a light intensity and the like, in the measured pulse wave signal. Further, the processor 120 may estimate blood pressure by using the obtained second pulse wave signal. In this case, a reference signal may be a signal obtained by performing nth-order ($n \geq 1$, with n being an integer) differentiation or integration on the first pulse wave signal.

Figure 2:
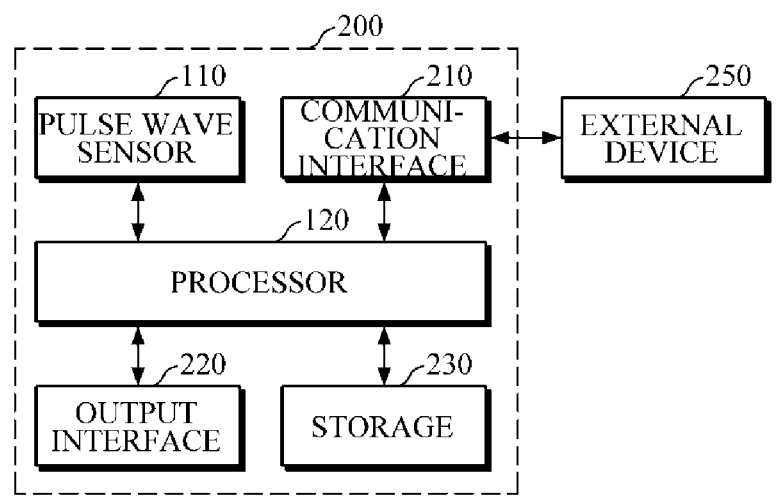
FIG. 2 is a block diagram illustrating an apparatus for estimating blood pressure according to embodiments.

FIG. 2 is a block diagram illustrating an apparatus 200 for estimating blood pressure according to embodiments.

Referring to FIG. 2, the blood pressure estimating apparatus 200 according to the embodiments further includes a communication interface 210, an output interface 220, and a storage 230, in addition to the pulse wave sensor 110 and the processor 120 of FIG. 1.

The pulse wave sensor 110 may be electrically connected to the processor 120, and may measure a pulse wave signal from a user under the control of the processor 120.

In response to a request for estimating blood pressure, the processor 120 may control the pulse wave sensor 110, and may control the communication interface 210, the output interface 220, the storage 230, and the like. Further, upon controlling the communication interface 210 to receive information for estimating blood pressure from an external device, the processor 120 may control the storage 230 to store the received information or may control the output interface 220 to output the information. In addition, the processor 120 may refer to the storage 230 to obtain information for estimating blood pressure, and may estimate blood pressure based on the obtained information.

The communication interface 210 may communicate with an external device 250 to transmit and receive various types of information associated with estimating blood pressure. In this case, examples of the external device 250 may include a blood pressure measuring device such as a cuff pressure measuring device, a pulse pressure measuring device, a medical device for measuring other types of bio-information, and an information processing device such as a smartphone, a tablet PC, a desktop computer, a laptop computer, and the like.

For example, the processor 120 may receive reference information, such as cuff pressure, a blood pressure estimation model, and the like that are for estimating blood pressure, from the external device 250. In addition, the processor 120 may transmit a pulse wave signal measured by the pulse wave sensor 110, a result of pulse wave analysis and a result of bio-information estimation that are generated by the processor 120, and the like, to the external device 250 such as a user's smartphone, a tablet PC, and the like.

The communication interface 210 may communicate with the external device 250 by using various wired or wireless communication techniques such as Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, these are examples and are not intended to be limiting.

The output interface 220 may provide the pulse wave signal measured by the pulse wave sensor 110, the estimation result of blood pressure, which is a processing result of the processor 120, and the like, to a user. For example, the output interface 220 may provide a user with information by various visual/non-visual methods using a visual output module such as a display and the like, a voice output module such as a speaker and the like, or a haptic module and the like through vibrations, tactile sensation, and the like.

The storage 230 may store various reference information for estimating blood pressure, the pulse wave signal measured by the pulse wave sensor 110, the estimation result of blood pressure generated by the processor 120, and the like. In this case, the reference information may include user characteristic information including a user's age, sex, health condition and the like, a reference blood pressure value obtained at a calibration time, a reference feature, a blood pressure estimation model, and the like.

The storage 230 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

Figure 3:
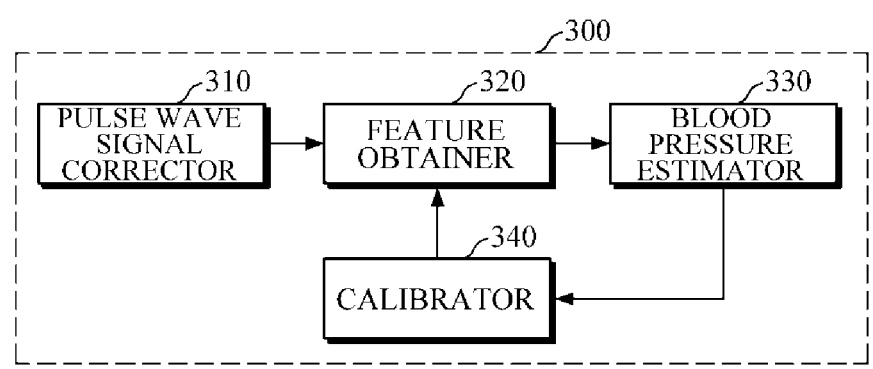
FIG. 3 is a block diagram illustrating an example of a processor of FIGS. 1 and 2.
Figure 4A:
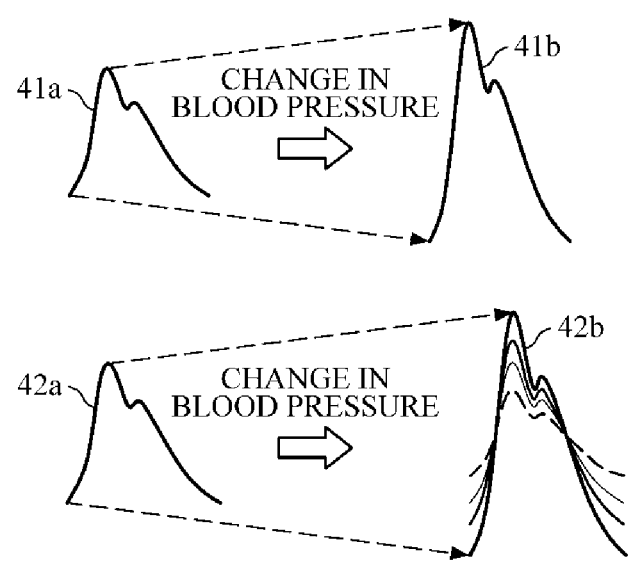
FIGS. 4A, 4B and 4C are diagrams explaining an example of estimating blood pressure, according to embodiments.
Figure 4B:
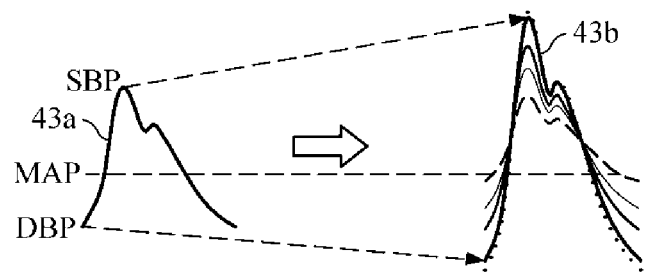
Figure 4C:
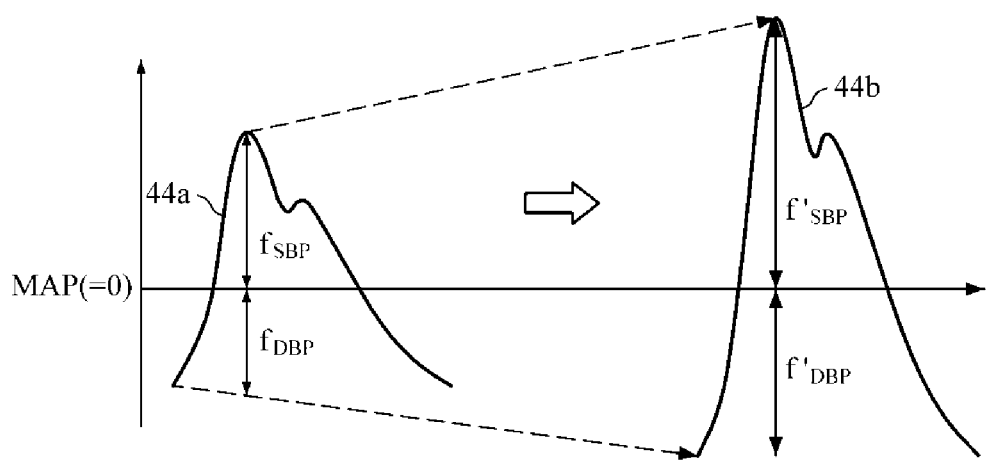

FIG. 3 is a block diagram illustrating an example of a processor of FIGS. 1 and 2. FIGS. 4A, 4B and 4C are diagrams explaining an example of estimating blood pressure, according to embodiments.

Referring to FIG. 3, a processor 300 includes a pulse wave signal corrector 310, a feature obtainer 320, a blood pressure estimator 330, and a calibrator 340.

Upon receiving the first pulse wave signal from the pulse wave sensor 110, the pulse wave signal corrector 310 may preprocess the received pulse wave signal. For example, the pulse wave signal corrector 310 may perform preprocessing, such as band-pass filtering between 0.5 Hz to 15 Hz, smoothing, bit equalization of continuously measured signals, and the like.

Further, upon receiving the first pulse wave signal, the pulse wave signal corrector 310 may obtain a second pulse wave signal by correcting the first pulse wave signal based on a reference signal, to compensate for a change in the waveform of the first pulse wave signal, which is caused by factors other than blood pressure.

For example, FIG. 4A illustrates similarity between waveforms 41a and 41b of a reference blood pressure and waveforms 42a and 42b of a pulse wave signal. As illustrated in FIG. 4A, similarly to a change in amplitude of the waveform 41b of the reference blood pressure measured at a blood pressure estimation time compared to the waveform 41a of the reference blood pressure in a stable state, an amplitude of the waveform 42b of the pulse wave signal measured at a blood pressure estimation time is changed compared to the waveform 42a of the pulse wave signal in a stable state. However, due to various factors, a variation of the waveforms 41a and 41b of the reference blood pressure is different from a variation of the waveforms 42a and 42b of the pulse wave signal, such that it is difficult to accurately estimate systolic blood pressure and diastolic blood pressure by using only the variation of the pulse wave signal waveforms 42a and 42b.

That is, an amplitude of the pulse wave signal based on an optical signal may be changed according to a light intensity, a user's characteristics, and the like, regardless of blood pressure, such that a measured amplitude or shape of the waveform 42b of the pulse wave signal obtained at a blood pressure estimation time may vary according to a user's characteristics, a light intensity, and the like. Accordingly, it is difficult to estimate blood pressure accurately by using only an absolute amplitude or a variation of the pulse wave signal waveform 42b.

Therefore, the pulse wave signal corrector 310 may generate a reference signal based on the first pulse wave signal; and upon generating the reference signal, the pulse wave signal corrector 310 may correct the first pulse wave signal by using the reference signal. For example, the pulse wave signal corrector 310 may generate the reference signal by differentiating or integrating the first pulse wave signal. In this case, the order of differentiation or integration is not specifically limited.

The change in the pulse wave signal waveform, which is caused by a light intensity, is also applied to a differentiated or integrated signal of the pulse wave signal. Accordingly, the pulse wave signal corrector 310 may compensate for a change in the first pulse wave signal waveform, caused by a light intensity and the like, by using the obtained differentiated or integrated signal.

The following Equation 1 represents an example of correcting the first pulse wave signal using the differentiated signal. The pulse wave signal corrector 310 may compensate for a change in the amplitude of the pulse wave signal, caused by a light intensity and the like, by normalizing the amplitude of the first pulse wave signal by dividing the amplitude of the first pulse wave signal by an amplitude of the differentiated signal, as represented by Equation 1. However, Equation 1 is an example, such that the correction is not limited thereto.

$$\frac{PP}{dPPGpp} = \frac{\alpha \times PP}{\alpha \times dPPGpp} \qquad \text{[Equation 1]}$$

Herein, PP denotes a difference in amplitude between a maximum point and an onset point of the first pulse wave signal, dPPGpp denotes a difference in amplitude between a maximum point and a minimum point of the first-order differentiated signal of the first pulse wave signal. Further, α denotes a change in the amplitude of the pulse wave signal waveform, caused by a factor other than blood pressure, e.g., a light intensity, compared to the pulse wave signal waveform in a stable state.

Upon normalizing the first pulse wave signal, the pulse wave signal corrector 310 may detect a predetermined reference point, e.g., any one or any combination of a point of mean arterial pressure (MAP), a point of systolic blood pressure (SBP), and a point of diastolic blood pressure (DBP), from the normalized pulse wave signal, and may obtain a second pulse wave signal by adjusting an offset of the normalized pulse wave signal based on the detected point.

FIG. 4B illustrates a waveform 43a of the normalized pulse wave signal in a stable state; and a waveform 43b of the normalized pulse wave signal at a blood pressure estimation time when blood pressure is changed. The following description will be made by referring to the waveform 43b of the normalized pulse wave signal at the blood pressure estimation time.

For example, based on MAP, SBP, and DBP values that are measured by an external blood pressure measuring device, the pulse wave signal corrector 310 may detect points, corresponding to the values, from the waveform 43b of the normalized pulse wave signal. In another example, the pulse wave signal corrector 310 may analyze the waveform 43b of the normalized pulse wave signal to detect a maximum point, an average point, and an onset point as points corresponding to SBP, MAP, and DBP respectively. In this case, the onset point may be a valley amplitude point in an analysis interval of the waveform 43b of the normalized pulse wave signal. Alternatively, the onset point may refer to points on a straight line formed by connecting a start point and an end point of the analysis interval. For example, an onset point at a time t may be a point corresponding to the time t on the straight line. The maximum point may be a peak amplitude point in the analysis interval. The average point may refer to a middle point between the onset point and the maximum point, or may be a point at which a ratio of an area between the maximum point and the average point to an area between the average point and the onset point is a predetermined ratio, e.g., 1:2.

FIG. 4C illustrates a waveform 44a of a second pulse wave signal in a stable state and a waveform 44b of a second pulse wave signal at a blood pressure estimation time. The following description will be made based on the waveform 44b of the second pulse wave signal at the blood pressure estimation time.

Referring to FIG. 4C, the pulse wave signal corrector 310 may obtain the waveform 44b of the second pulse wave signal by adjusting an offset of the detected point, e.g., the waveform of the pulse wave signal that is normalized so that a MAP value becomes 0.

Once the pulse wave signal corrector 310 obtains the waveform 44b of the second pulse wave signal, the feature obtainer 320 may obtain a feature for estimating blood pressure based on the waveform 44b of the second pulse wave signal. Further, the feature obtainer 320 may normalize the feature, obtained for estimating blood pressure, based on a feature at a calibration time.

For example, based on a difference between a systolic blood pressure point (e.g., maximum point) and an average blood pressure point (e.g., average point) of the waveform 44b of the second pulse wave signal, the feature obtainer 320 may obtain a feature $f'_{SBP}$ for systolic blood pressure. Further, based on a difference between the average blood pressure point (e.g., average point) and a diastolic blood pressure point (e.g., onset point), the feature obtainer 320 may obtain a feature $f'_{DBP}$ for diastolic blood pressure.

As described above, upon obtaining the feature $f'_{SBP}$ for systolic blood pressure and the feature $f'_{DBP}$ for diastolic blood pressure for estimating blood pressure, the feature obtainer 320 may normalize the feature $f'_{SBP}$ for systolic blood pressure and the feature $f'_{DBP}$ for diastolic blood pressure by dividing the obtained features $f'_{SBP}$ and $f'_{DBP}$ by a reference feature $f_{SBP}$ for systolic blood pressure and a reference feature $f_{DBP}$ for diastolic blood pressure respectively, which are obtained from the waveform 44a of the second pulse wave signal at a calibration time, as represented by the following Equation 2.

$$\Delta f_{BP} = f'_{BP}/f_{BP} \qquad \text{[Equation 2]}$$

Herein, BP denotes systolic blood pressure SBP and diastolic blood pressure DBP; and $\Delta f_{BP}$ denotes the normalized feature, and a variation of the feature $f'_{BP}$ obtained at the blood pressure estimation time compared to the feature $f_{BP}$ obtained at a calibration time.

The blood pressure estimator 330 may obtain a blood pressure variation based on the features normalized by the feature obtainer 320, and may estimate blood pressure based on the obtained blood pressure variation. The following Equation 3 represents an example of an equation for estimating a blood pressure variation. However, this is an example, and the equation is not limited thereto.

$$\Delta SBP = (SBP_c - MAP_c) \times \Delta f_{SBP}$$

$$\Delta DBP = (MAP_c - DBP_c) \times \Delta f_{SBP} \qquad \text{[Equation 3]}$$

Herein, ΔSBP denotes a variation in systolic blood pressure compared to the calibration time; ΔDBP denotes a variation in diastolic blood pressure compared to the calibration time; $SBP_c$, $MAP_c$, $DBP_c$ denote systolic blood pressure, mean arterial pressure, and diastolic blood pressure at the calibration time respectively, and may be values measured by an external blood pressure measuring device such as a cuff pressure measuring device; and $\Delta f_{SBP}$ and $\Delta f_{DBP}$ may be the normalized feature for systolic blood pressure and the normalized feature for diastolic blood pressure, which are normalized using the above Equation 2.

Further, upon estimating the blood pressure variation, the blood pressure estimator 330 may estimate blood pressure based on a reference blood pressure. In this case, the reference blood pressure may be mean arterial pressure measured by a blood pressure measuring device at the calibration time. The following Equation 4 may be an example of a blood pressure estimation model that defines a correlation between an estimated blood pressure value, a blood pressure variation, and a reference blood pressure, and is an example of a linear combination equation, but is not limited thereto.

$$SBP_{est}=MAP_c+\Delta SBP$$

$$DBP_{est}=MAP_c-\Delta DBP \qquad \text{[Equation 4]}$$

Herein, $SBP_{est}$ and $DBP_{est}$ each denote an estimated systolic blood pressure value and an estimate diastolic blood pressure value to be obtained; $\Delta SBP$ and $\Delta DBP$ denote a variation in systolic blood pressure and a variation in diastolic blood pressure respectively; and $MAP_c$ and $DBP_c$ denote mean arterial pressure and diastolic blood pressure at the calibration time respectively, and may be values measured by an external blood pressure measuring device such as a cuff-type blood pressure measuring device.

The calibrator 340 may perform calibration at predetermined intervals, or in response to analysis of a blood pressure estimation result or a user's request. Upon determining to perform calibration, the calibrator 340 may control the pulse wave sensor 110 to obtain a pulse wave signal for calibration.

Further, the calibrator 340 may control the communication interface 210 of FIG. 2 to receive reference information at the calibration time from an external device 250, for example, information such as cuff systolic blood pressure, cuff diastolic blood pressure, and the like from a cuff-type blood pressure measuring device. In this case, the calibrator 340 may guide a user to touch the pulse wave sensor 110 with an object, may provide guidance on connection to the external device 250 through the communication interface 210, or may guide a user to measure reference bio-information through the external device 250.

If connection to the external device 250 is not made via the communication interface 210, the calibrator 340 may provide an interface to a user through the output interface 220, and may receive reference information from the user through the interface.

Once the pulse wave sensor 110 measures the pulse wave signal for calibration, the calibrator 340 may correct the pulse wave signal by analyzing the measured pulse wave signal for calibration as described above, and may obtain a reference feature from the corrected pulse wave signal and store the reference feature in the storage 230 as reference information.

Figure 5:
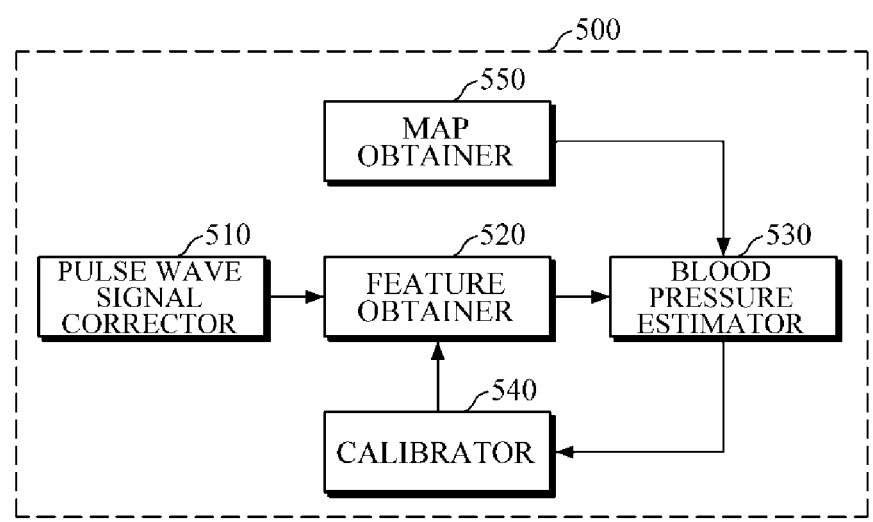
FIG. 5 is a block diagram illustrating another example of the processor of FIGS. 1 and 2, according to embodiments.

FIG. 5 is a block diagram illustrating another example of the processor of FIGS. 1 and 2, according to embodiments.

Referring to FIG. 5, a processor 500 according to the embodiments includes a pulse wave signal corrector 510, a feature obtainer 520, a blood pressure estimator 530, a calibrator 540, and a MAP obtainer 550.

Once the pulse wave sensor 110 measures a first pulse wave signal for estimating blood pressure, the pulse wave signal corrector 510 may obtain a second pulse wave signal by correcting the measured first pulse wave signal, which is described above in detail with reference to FIGS. 3 to 4C, such that description thereof will be omitted. However, in the case of estimating blood pressure by using features associated with pulse pressure that will be described below, the process of adjusting an offset described above may be omitted.

Once the pulse wave signal corrector 510 obtains a waveform of the second pulse wave signal, the feature obtainer 520 may obtain a feature for estimating blood pressure based on the waveform of the second pulse wave signal. Further, the feature obtainer 520 may normalize the obtained feature for estimating blood pressure based on a feature at a calibration time.

For example, the feature obtainer 520 may obtain a feature associated with pulse pressure (PP) by analyzing the waveform of the second pulse wave signal. The feature obtainer 520 may obtain the feature associated with pulse pressure by using an equation such as the following Equation 5 based on relevance of a difference between systolic blood pressure and diastolic blood pressure to pulse pressure.

$$f_{PP}=f_{SBP}+f_{DBP} \qquad \text{[Equation 5]}$$

That is, the feature obtainer 520 may obtain the feature $f_{PP}$ associated with pulse pressure by adding the obtained feature $f_{SBP}$ for systolic blood pressure and the obtained feature $f_{DBP}$ for diastolic blood pressure described above.

In addition, upon obtaining the feature $f_{PP}$ associated with pulse pressure, the feature obtainer 520 may obtain a variation of the feature $f_{PP}$ associated with pulse pressure by normalizing the feature $f_{PP}$ associated with pulse pressure based on a feature $f_{PP}$ associated with pulse pressure at the calibration time that is pre-obtained by the calibrator 540.

Further, the MAP obtainer 550 may obtain an estimated mean arterial pressure value. The MAP obtainer 550 may obtain mean arterial pressure, estimated by an external device at a blood pressure estimation time, from the external device. Alternatively, the MAP obtainer 550 may estimate an MAP value by using a bio-signal alone, which is measured by a bio-signal sensor (e.g. an electrocardiogram sensor, a ballistocardiogram sensor, etc.) separately mounted in the blood pressure estimating apparatuses 100 and 200 in addition to the pulse wave sensor 110, or by using the bio-signal in combination with a pulse wave signal based on a method of pulse wave velocity (PWV), a method of pulse transit time (PTT) analysis, and the like. The MAP obtainer 550 may be provided as a function of the blood pressure estimator 530 that will be described below.

Once the feature obtainer 520 obtains the variation of the feature associated with pulse pressure, the blood pressure estimator 530 may estimate pulse pressure based on the variation of the feature associated with pulse pressure and a reference pulse pressure at the calibration time. The following Equation 6 represents an example of a mathematical function for estimating pulse pressure, but the equation is not limited thereto.

$$PP_{est}=PP_c \times \Delta f_{PP} \qquad \text{[Equation 6]}$$

Herein, $PP_{est}$ denotes an estimated pulse pressure value, and $PP_c$ denotes a reference pulse pressure value at the calibration time. The reference pulse pressure value may be obtained from an external pulse pressure measuring device at the calibration time; or a value, obtained by subtracting a diastolic blood pressure value from a systolic blood pressure value measured by an external blood pressure measuring device at the calibration time, may be defined as the reference pulse pressure value. However, the reference pulse pressure value is not limited thereto, and may be obtained by analyzing the pulse wave signal at the calibration time, or by analyzing other bio-signals, such as electrocardiogram and the like, which are obtained by other bio-signal sensors from a user at the calibration time.

Upon obtaining the estimated pulse pressure value, the blood pressure estimator 530 may estimate blood pressure based on the estimated MAP value obtained by the MAP obtainer 550 and the estimated pulse pressure value. For example, the blood pressure estimator 530 may estimate blood pressure using Equation 7 that defines a relationship between MAP, PP, DBP, and SBP. However, the equation is not limited thereto, and blood pressure may also be estimated using various blood pressure estimation models predefined by various methods such as linear/nonlinear regression analysis, neural network, deep learning, and the like.

$$MAP = DBP + \frac{PP}{3}$$ [Equation 7]

$$PP = SBP - DBP$$

Herein, MAP denotes the estimated MAP value obtained as described above, PP denotes the estimated pulse pressure value; and SBP and DBP denote the SBP value and the DBP value to be obtained.

The calibrator 540 may monitor whether calibration is to be performed as described above; and upon monitoring that calibration is to be performed, the calibrator 40 may perform an operation for calibration. Further, once the pulse wave signal for calibration is measured, the calibrator 540 may calibrate the pulse wave signal, and may obtain a feature associated with a reference pulse wave at the calibration time based on the calibrated pulse wave signal.

In embodiments, instead of using the feature associated with pulse pressure, the blood pressure estimator 530 may obtain a variation of the feature for systolic blood pressure and a variation of the feature for diastolic blood pressure as described above with reference to FIG. 3, and may estimate blood pressure by using the obtained variations and the estimated MAP value obtained by the MAP obtainer 550. That is, by inputting the estimated MAP value, instead of the reference MAP value $MAP_c$, into the above Equation 4, the blood pressure estimator 530 may obtain SBP and DBP.

Figure 6:
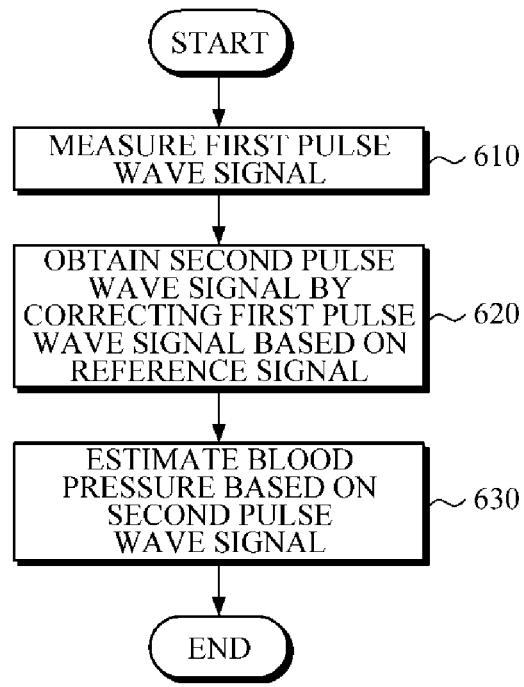
FIG. 6 is a flowchart illustrating a method of estimating blood pressure, according to embodiments.
Figure 7:
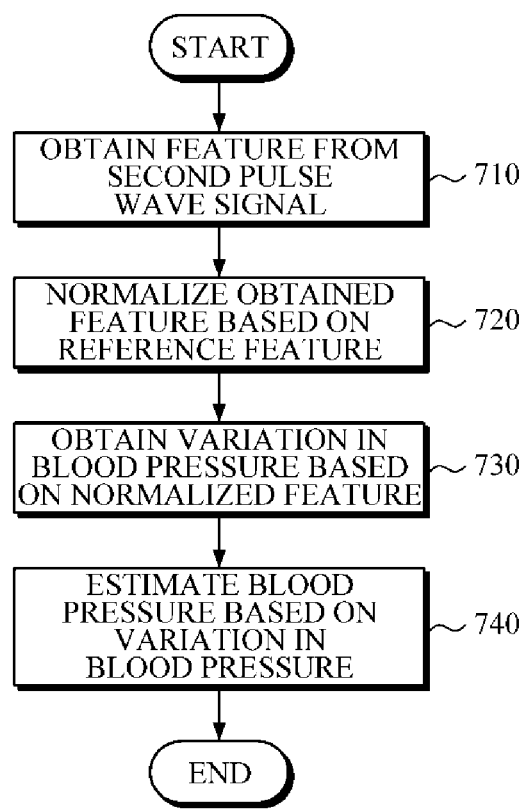
FIGS. 7 and 8 are flowcharts illustrating examples of estimating of blood pressure of FIG. 6.
Figure 8:
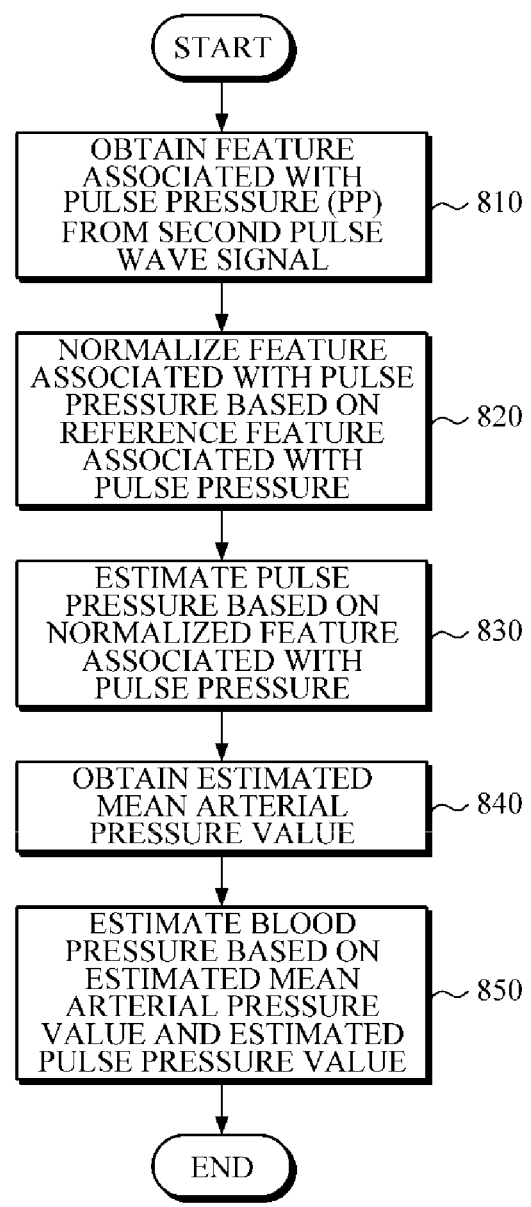

FIG. 6 is a flowchart illustrating a method of estimating blood pressure, according to embodiments. FIGS. 7 and 8 are flowcharts illustrating examples of estimating of blood pressure of FIG. 6.

The estimating of blood pressure of FIG. 6 may be performed by the blood pressure estimating apparatuses 100 and 200 according to embodiments of FIG. 1 or 2.

In response to a request for estimating blood pressure, the blood pressure estimating apparatus may drive the pulse wave sensor to measure a first pulse wave signal for estimating blood pressure in operation 610. The request for estimating blood pressure may be input by a user or may be received from a connected external device. Alternatively, for continuous estimation of blood pressure, the request for estimating blood pressure may be generated at predetermined intervals or may be generated automatically in the blood pressure estimating apparatus according to predetermined factors such as a change in external environment and the like. In this case, the pulse wave signal may include any one or any combination of a photoplethysmogram (PPG) signal, an impedance plethysmogram (IPG) signal, and a video plethysmogram (VPG) signal.

Then, the blood pressure estimating apparatus may obtain a second pulse wave signal by correcting the first pulse wave signal based on a reference signal in operation 620. For example, the blood pressure estimating apparatus may obtain the reference signal by differentiating or integrating the first pulse wave signal, and may normalize an amplitude of the first pulse wave signal by dividing the amplitude of the first pulse wave signal by an amplitude of the reference signal. Further, the blood pressure estimating apparatus may obtain the second pulse wave signal by adjusting an offset of the pulse wave signal that is normalized so that a value of a predetermined reference point, e.g., a point of MAP, becomes 0.

Subsequently, the blood pressure estimating apparatus may estimate blood pressure based on the second pulse wave signal in operation 630.

Referring to FIG. 7, the estimating of blood pressure in operation 630 will be described below.

The blood pressure estimating apparatus may obtain a feature for estimating blood pressure from the second pulse wave signal in operation 710. For example, the blood pressure estimating apparatus may obtain a feature for systolic blood pressure based on a difference between a point of MAP and a point of SBP, and may obtain a feature for diastolic blood pressure based on a difference between a point of MAP and a point of DBP.

Then, the blood pressure estimating apparatus may normalize the obtained feature based on a reference feature in operation 720. In this case, the reference feature may be obtained based on the second pulse wave signal, which is obtained by correcting the first pulse wave signal for calibration at the calibration time. In addition, the reference feature includes a reference feature for systolic blood pressure and a reference feature for diastolic blood pressure, and upon obtaining the feature for systolic blood pressure and the feature for diastolic blood pressure in operation 710, the blood pressure estimating apparatus may normalize the obtained features by dividing the features by the reference feature for systolic blood pressure and the reference feature for diastolic blood pressure respectively.

Subsequently, the blood pressure estimating apparatus may obtain a variation in blood pressure based on the normalized feature and the reference blood pressure in operation 730. For example, the blood pressure estimating apparatus may obtain a variation in systolic blood pressure by multiplying a difference between a reference systolic blood pressure and a reference mean arterial pressure, which are measured at the calibration time by an external blood pressure measuring device, by the normalized feature for systolic blood pressure. Further, the blood pressure estimating apparatus may obtain a variation in diastolic blood pressure by multiplying a difference between a reference diastolic blood pressure and a reference mean arterial pressure by the normalized feature for diastolic blood pressure.

Next, the blood pressure estimating apparatus may estimate blood pressure based on the variation in blood pressure in operation 740. For example, the blood pressure estimating apparatus may estimate systolic blood pressure by adding the variation in systolic blood pressure to the reference mean arterial pressure, and may estimate diastolic blood pressure by subtracting the variation in diastolic blood pressure from the reference mean arterial pressure. However, the estimation of blood pressure is not limited thereto, and the blood pressure estimating apparatus may estimate blood pressure by applying various other blood pressure estimation models.

In addition, a bio-signal, such as electrocardiogram (ECG), ballistocardiogram (BCG), and the like, may be obtained using an external sensor, and the blood pressure estimating apparatus may obtain an estimated mean arterial pressure value at the blood pressure estimation time by using the obtained bio-signals. Further, the blood pressure estimating apparatus may also estimate blood pressure by using the variation of blood pressure and the estimated mean arterial pressure value.

Referring to FIG. 8, the estimating of blood pressure in operation 630 will be described below.

The blood pressure estimating apparatus may obtain a feature associated with pulse pressure (PP) for estimating blood pressure from the second pulse wave signal in operation 810. For example, the blood pressure estimating apparatus may obtain a feature for systolic blood pressure and a feature for diastolic blood pressure by using the second pulse wave signal, and may obtain the feature associated with pulse pressure by adding the obtained feature for systolic blood pressure and the obtained feature for diastolic blood pressure together.

Then, the blood pressure estimating apparatus may normalize the obtained feature associated with pulse pressure based on a reference feature associated with pulse pressure in operation 820. In this case, the reference feature associated with pulse pressure may be obtained based on the second pulse wave signal that is obtained by correcting the first pulse wave signal for calibration at the calibration time. Upon obtaining the feature associated with pulse pressure in operation 810, the blood pressure estimating apparatus may normalize the feature associated with pulse pressure by dividing the feature associated with pulse pressure by the reference feature at the calibration time.

Subsequently, the blood pressure estimating apparatus may estimate pulse pressure based on the normalized feature associated with pulse pressure and a reference pulse pressure in operation 830. For example, the blood pressure estimating apparatus may obtain the reference pulse pressure by subtracting the obtained diastolic blood pressure from the obtained systolic blood pressure, which are measured at the calibration time by an external blood pressure measuring device, and may estimate pulse pressure by multiplying the normalized feature associated with pulse pressure by the reference pulse pressure.

Next, the blood pressure estimating apparatus may obtain an estimated mean arterial pressure value in operation 840. In this case, the estimated mean arterial pressure value may be a mean arterial pressure value estimated based on the second pulse wave signal and/or a bio-signal, such as electrocardiogram (ECG), ballistocardiogram (BCG), and the like, which is measured by an external sensor. The operation 830 and the operation 840 may be performed regardless of the order.

Then, the blood pressure estimating apparatus may estimate blood pressure based on the estimated pulse pressure value and the estimated mean arterial pressure value in operation 850. For example, the blood pressure estimating apparatus may estimate systolic blood pressure and diastolic blood pressure by applying a blood pressure estimating model that defines a relationship between pulse pressure, mean arterial pressure, systolic blood pressure, and diastolic blood pressure, as represented by the above Equation 7.

Figure 9:
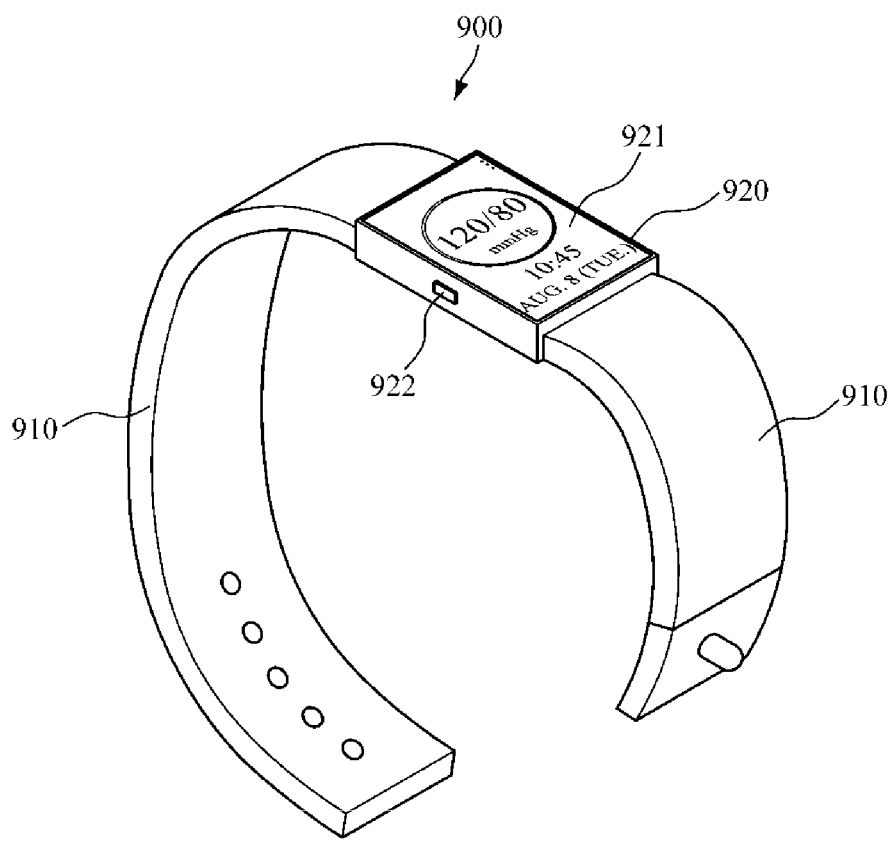
FIG. 9 is a diagram illustrating a wearable device according to embodiments.

FIG. 9 is a diagram illustrating a wrist-type wearable device 900 according to embodiments.

Referring to FIG. 9, the wrist-type wearable device 900 includes a strap 910 and a main body 920.

The strap 910 may be connected to both ends of the main body 920 to be fastened in a detachable manner or may be integrally formed therewith as a smart band. The strap 910 may be made of a flexible material to be wrapped around a user's wrist so that the main body 920 may be worn on the wrist.

The main body 920 may include the blood pressure estimating apparatuses 100 and 200 described above. For example, a pulse wave sensor for measuring a pulse wave signal from a user's wrist may be mounted in the main body 920. In this case, the pulse wave sensor may be a photoplethysmogram (PPG) sensor that emits light onto the user's wrist, and detects light returning from the user's wrist. However, the sensor is not limited thereto, and may be an impedance plethysmogram (IPG) sensor, a video plethysmogram (VPG) sensor, and the like.

Further, the main body 920 may include a processor that is electrically connected to the pulse wave sensor and measures blood pressure as described above. In addition, the main body 920 may also include a communication interface for communicating with an external device, and a storage for storing information associated with estimating blood pressure and other information for performing functions of the wearable device.

A battery, which supplies power to the wrist-type wearable device 900, may be embedded in the main body 920.

The wrist-type wearable device 900 may further include a display 921 and a manipulator 922 that are mounted at the main body 920. The display 921 may display data processed by the wrist-type wearable device 900, processing result data thereof, and the like. The display 921 may include a touch screen that allows touch input, and may receive a touch input from a user and transmit the received input to the processor.

The manipulator 922 may receive input of various control signals from a user. The manipulator 922 may include a power button to turn on/off the wrist-type wearable device 900.

The embodiments can be realized as a computer-readable code written on a non-transitory computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments for realizing the embodiments can be easily deduced by one of ordinary skill in the art.

The inventive concepts have been described herein with regard to the embodiments. However, it will be obvious to those skilled in the art that various changes and modifications can be made without changing technical ideas and features of the disclosure. Thus, it is clear that the above-described embodiments are illustrative in all aspects and are not intended to limit the disclosure.

What is claimed is:

1. An apparatus implemented in a wearable device worn by a user for continuously estimating blood pressure of the user, the apparatus comprising:
    a pulse wave sensor, including a light sensor, configured to measure a first pulse wave signal at a time of estimating the blood pressure from the user;
    a processor configured to:
        differentiate or integrate the measured first pulse wave signal to obtain a reference signal;

correct the measured first pulse wave signal, based on the obtained reference signal, to obtain a second pulse wave signal, wherein correcting the measured first pulse wave signal adjusts for changing light intensity of an environment of the apparatus detected by the light sensor; and estimate the blood pressure of the user, based on the obtained second pulse wave signal and a third pulse wave signal measured at a calibration time when the user is in a stable state, different from the time of estimating the blood pressure to provide a continuous blood pressure condition of the user; and a display configured to display the estimated blood pressure of the user.

2. The apparatus of claim 1, wherein to correct the measured first pulse wave signal, the processor is further configured to:

divide an amplitude of the measured first pulse wave signal by an amplitude of the obtained reference signal to normalize the amplitude of the measured first pulse wave signal; and adjust an offset of the first pulse wave signal of which the amplitude is normalized, based on a predetermined reference point of the first pulse wave signal of which the amplitude is normalized, to obtain the second pulse wave signal.

3. The apparatus of claim 2, wherein the predetermined reference point comprises any one or any combination of a point of mean arterial pressure (MAP), a point of systolic blood pressure (SBP), and a point of diastolic blood pressure (DBP) of the first pulse wave signal of which the amplitude is normalized.

4. The apparatus of claim 1, wherein the processor is further configured to:

obtain a feature for estimating the blood pressure, from the obtained second pulse wave signal; and normalize the obtained feature, using a reference feature, the reference feature being obtained from the third pulse wave signal measured at the time of calibration of the apparatus.

5. The apparatus of claim 4, wherein the processor is further configured to:

obtain a feature for systolic blood pressure (SBP), based on a difference between a value of the SBP and a value of mean arterial pressure (MAP) of the obtained second pulse wave signal; and obtain a feature for diastolic blood pressure (DBP), based on a difference between the value of the MAP and a value of the DBP of the obtained second pulse wave signal.

6. The apparatus of claim 4, wherein the processor is further configured to:

obtain a variation in the blood pressure, based on the normalized obtained feature; and estimate the blood pressure, based on the obtained variation in the blood pressure.

7. The apparatus of claim 6, wherein the processor is further configured to:

multiply a difference between a reference systolic blood pressure (SBP) and a reference mean arterial pressure (MAP) by a normalized feature for SBP of the obtained second pulse wave signal, to obtain a variation in the SBP, wherein the reference SBP and the reference MAP are determined at the time of calibration of the apparatus; and multiply a difference between the reference MAP and a reference diastolic blood pressure (DBP) by a normalized feature for DBP of the obtained second pulse wave signal, to obtain a variation in the DBP, wherein the reference DBP is determined at the time of calibration of the apparatus.

8. The apparatus of claim 6, wherein the processor is further configured to estimate the blood pressure, based on the obtained variation in the blood pressure and a reference mean arterial pressure (MAP) at the time of the calibration of the apparatus.

9. The apparatus of claim 6, wherein the processor is further configured to:

obtain a mean arterial pressure (MAP) estimation value at the time of estimating the blood pressure; and estimate the blood pressure, based on the obtained MAP estimation value and the obtained variation in the blood pressure.

10. The apparatus of claim 1, wherein the processor is further configured to:

monitor whether calibration of the apparatus relative to an external reference apparatus is to be performed; and based on the monitoring indicating that calibration is to be performed, obtain a reference feature, wherein the reference feature comprises at least one of a reference mean arterial pressure (MAP), a reference systolic blood pressure (SBP), and a reference diastolic blood pressure (DBP).

11. An apparatus implemented in a wearable device worn by a user for continuously estimating blood pressure, the apparatus comprising:

a pulse wave sensor, including a light sensor, configured to measure a first pulse wave signal at a time of estimating the blood pressure from a user;

a processor configured to:

differentiate or integrate the measured first pulse wave signal to obtain a reference signal;

correct the measured first pulse wave signal, based on the obtained reference signal, to obtain a second pulse wave signal, wherein correcting the measured first pulse wave signal adjusts for changing light intensity of an environment of the wearable device detected by the light sensor;

obtain a feature associated with pulse pressure (PP), based on the obtained second pulse wave signal; and estimate the blood pressure of the user, based on the obtained feature associated with the PP and a reference feature associated with the PP obtained at a calibration time when the user is in a stable state, different from the time of estimating the blood pressure to provide a continuous blood pressure condition of the user; and a display configured to display the estimated blood pressure of the user.

12. The apparatus of claim 11, wherein to correct the measured pulse wave signal, the processor is further configured to:

divide an amplitude of the measured first pulse wave signal by an amplitude of the obtained reference signal, to normalize the amplitude of the measured first pulse wave signal; and obtain the second pulse wave signal, based on the first pulse wave signal of which the amplitude is normalized.

13. The apparatus of claim 11, wherein the processor is further configured to normalize the obtained feature associated with the PP, using the reference feature associated with pulse pressure at the time of calibration of the apparatus.

14. The apparatus of claim 13, wherein the processor is further configured to estimate the PP, based on the normalized feature associated with the PP and the pulse pressure at the time of calibration of the apparatus.

15. The apparatus of claim 14, wherein the processor is further configured to:
   obtain a mean arterial pressure (MAP) estimation value at a time of estimating the blood pressure; and
   estimate the blood pressure, based on the obtained MAP estimation value and the estimated PP.

16. The apparatus of claim 11, wherein the processor is further configured to:
   obtain a feature for systolic blood pressure (SBP) and a feature for diastolic blood pressure (DBP), based on the obtained second pulse wave signal; and
   obtain the feature associated with the PP, based on the obtained feature for the SBP and the obtained feature for the DBP.

17. A method of continuously estimating blood pressure via a wearable device, the method comprising:
   while the wearable device is worn by a user, measuring a first pulse wave signal, using a pulse wave sensor including a light sensor, from the user at a time of estimating the blood pressure;
   differentiating or integrating the measured first pulse wave signal to obtain a reference signal;
   correcting the measured first pulse wave signal, based on the obtained reference signal, to obtain a second pulse wave signal, wherein correcting the measured first pulse wave signal adjusts for changing light intensity of an environment of the wearable device based on measurements of the light sensor;
   estimating the blood pressure, based on the obtained second pulse wave signal and a pulse wave signal measured at a calibration time when the user is in a stable state, different from the time of estimating the blood pressure to provide a continuous blood pressure condition of the user; and
   displaying information of the estimated blood pressure on the wearable device.

18. The method of claim 17, wherein correcting the measured first pulse wave signal further comprises dividing an amplitude of the measured first pulse wave signal by an amplitude of the obtained reference signal, to normalize the amplitude of the measured first pulse wave signal,
   and adjusting an offset of the first pulse wave signal of which the amplitude is normalized, based on a predetermined reference point of the first pulse wave signal of which the amplitude is normalized, to obtain the second pulse wave signal.

19. The method of claim 17, further comprising:
   obtaining a feature for estimating the blood pressure, from the obtained second pulse wave signal; and
   normalizing the obtained feature, using a reference feature that is obtained at the time of calibration of the wearable device.

20. The method of claim 19, further comprising obtaining a variation in the blood pressure, based on the normalized feature,
   wherein the estimating of the blood pressure is further based on the obtained variation in the blood pressure.

* * * * *